United States Patent [19]
Parikh et al.

[11] Patent Number: 5,948,437
[45] Date of Patent: Sep. 7, 1999

[54] PHARMACEUTICAL COMPOSITIONS USING THIAZEPINE

[75] Inventors: Bhavnish Vinod Parikh, Hockessin, Del.; Robert Joseph Timko, West Chester, Pa.; William Joseph Addicks, Morgantown, W. Va.

[73] Assignee: Zeneca Limited, United Kingdom

[21] Appl. No.: 08/864,306

[22] Filed: May 28, 1997

Related U.S. Application Data

[60] Provisional application No. 60/018,816, May 31, 1996.

[51] Int. Cl.$^6$ ............................................. A61K 9/20
[52] U.S. Cl. ........................ 424/464; 424/470; 424/458; 514/211
[58] Field of Search .................................. 424/464, 401; 514/211; 540/551

[56] References Cited

U.S. PATENT DOCUMENTS

| | | |
|---|---|---|
| 3,065,143 | 11/1962 | Christenson et al. . |
| 3,590,117 | 6/1971 | Christenson et al. . |
| 3,870,790 | 3/1975 | Lowey et al. . |
| 4,226,849 | 10/1980 | Schor . |
| 4,259,314 | 3/1981 | Lowey . |
| 4,309,406 | 1/1982 | Guley et al. . |
| 4,357,469 | 11/1982 | Schor . |
| 4,369,172 | 1/1983 | Schor et al. . |
| 4,389,393 | 6/1983 | Schor et al. . |
| 4,540,566 | 9/1985 | Davis et al. . |
| 4,680,323 | 7/1987 | Lowey . |
| 4,734,285 | 3/1988 | Alderman . |
| 4,795,327 | 1/1989 | Gaylord et al. . |
| 4,849,229 | 7/1989 | Gaylord et al. . |
| 4,871,548 | 10/1989 | Edgren et al. . |
| 4,879,288 | 11/1989 | Warawa et al. ................ 514/211 |
| 4,919,938 | 4/1990 | Lovegrove et al. . |
| 5,126,145 | 6/1992 | Evenstad et al. . |
| 5,393,765 | 2/1995 | Infeld et al. . |
| 5,419,918 | 5/1995 | Lundberg . |

FOREIGN PATENT DOCUMENTS

| | | |
|---|---|---|
| 8663947 | 4/1987 | Australia . |
| 111144 | 6/1984 | European Pat. Off. . |
| 157695 | 10/1985 | European Pat. Off. . |
| 236002 | 9/1987 | European Pat. Off. . |
| 253541 | 1/1988 | European Pat. Off. . |
| 284849 A1 | 10/1988 | European Pat. Off. . |
| 325086 | 7/1989 | European Pat. Off. . |
| 284849 B1 | 8/1993 | European Pat. Off. . |
| 2604902 | 4/1988 | France . |
| 3733540 | 4/1988 | Germany . |
| 52-145514 | 12/1977 | Japan . |
| 60-185728 | 9/1985 | Japan . |
| 62-149632 | 7/1987 | Japan . |
| 63-5982 | 1/1988 | Japan . |
| 63-101334 | 5/1988 | Japan . |
| 4-82826 | 3/1992 | Japan . |
| 6-172161 | 6/1994 | Japan . |
| 78/5528 | 11/1979 | South Africa . |
| 1430684 | 3/1976 | United Kingdom . |
| 1583801 | 2/1981 | United Kingdom . |
| 2195893 | 4/1988 | United Kingdom . |
| 2219206 | 12/1989 | United Kingdom . |
| WO 85/04100 | 9/1985 | WIPO . |
| WO 87/00044 | 1/1987 | WIPO . |
| WO 92/04013 | 3/1992 | WIPO . |
| WO 92/10169 | 6/1992 | WIPO . |

*Primary Examiner*—Thurman K. Page
*Assistant Examiner*—William E. Benston, Jr.

[57] ABSTRACT

The invention relates to sustained release formulations comprising 11-[4-[2-(2-hydroxyethoxy)ethyl]-1-piperazinyl]dibenzo[b,f] [1,4]thiazepine or a pharmaceutically acceptable salt thereof, to methods of treating psychotic states and hyperactivity utilizing the sustained release formulations and to a process for preparing the sustained release formulations.

15 Claims, 2 Drawing Sheets

PHARMACEUTICAL COMPOSITIONS USING THIAZEPINE

This application claims the benefit of U.S. Provisional Application No. 60/018,816, filed on May 31, 1996.

The present invention relates to a pharmaceutical composition and more particularly to a sustained release pharmaceutical composition comprising 11-[4-[2-(2-hydroxyethoxy)ethyl]-1-piperazinyl]dibenzo[b,f][1,4] thiazepine or a pharmaceutically acceptable salt thereof.

It is desirable in the treatment of a number of diseases, both therapeutically and prophylactically, to provide the active pharmaceutical ingredient in a sustained release form. Desirably the sustained release provides a generally uniform and constant rate of release over an extended period of time which achieves a stable and desired blood (plasma) level of the active ingredient without the need for frequent administration of the medicament.

While there are numerous sustained release formulations known in the art which utilize gelling agents, such as hydroxypropyl methylcelluloses, it has been found to be difficult to formulate sustained release formulations of soluble medicaments and gelling agents, such as hydroxypropyl methylcellulose, for several reasons. First of all, active ingredients which are soluble in water tend to generate a sustained release product which is susceptible to a phenomenon known as dose dumping. That is, release of the active ingredient is delayed for a time but once release begins to occur the rate of release is very high. Moreover, fluctuations tend to occur in the plasma concentrations of the active ingredient which increases the likelihood of toxicity. Further, some degree of diurnal variation in plasma concentration of the active ingredient has also been observed. Finally, it has been found to be difficult to achieve the desired dissolution profiles or to control the rate of release of the soluble medicament.

Accordingly, a need exists for sustained release formulations of soluble medicaments, such as, 11-[4-[2-(2-hydroxyethoxy)ethyl]-1-piperazinyl]dibenzo[b,f][1,4] thiazepine or a pharmaceutically acceptable salt, which overcome, or at least alleviate, one or more of the above described difficulties and which further provide the advantageous property of allowing the active medicament to be administered less frequently, e.g. once a day, while achieving blood (plasma) levels similar to those attained by administering smaller doses of the medicament more frequently, e.g. two or more times daily.

The compound, 11-[4-[2-(2-hydroxyethoxy)ethyl]-1-piperazinyl]-dibenzo[b,f][1,4]thiazepine (see Formula I below), and its pharmaceutically acceptable salts exhibit useful antidopaminergic activity and may be used, for

I $CH_2CH_2OCH_2CH_2CH$ example, as an antipsychotic agent (for example, for the management of the manifestations of psychotic disorders) or as a treatment for hyperactivity. It is a compound of particular interest since it may be used as an antipsychotic agent with a substantial reduction in the potential to cause side effects such as acute dystonia, acute dyskinesia, pseudo-Parkinsonism and tardive dyskinesia which side-effects may result from the use of other antipsychotics or neuroleptics.

The preparation, physical properties and beneficial pharmacological properties of 11 -[4-[2-(2- hydroxyethoxy) ethyl]-1 -piperazinyl]dibenzo[b,f][1,4]-thiazepine, and its pharmaceutically acceptable salts are described in published European Patents EP 240,228 and 282,236 as well as in U.S. Pat. No. 4,879,288, the entire contents of which are herein incorporated by reference.

According to the present invention there is provided a sustained release formulation comprising a gelling agent, preferably hydroxypropyl methylcellulose, and 11-[4-[2-(2-hydroxyethoxy)ethyl]-1-piperazinyl]dibenzo-[b,f][1,4] thiazepine, or a pharmaceutically acceptable salt thereof, together with one or more pharmaceutically acceptable excipients. Preferably, the sustained release formulation comprises a hydrophilic matrix comprising a gelling agent, preferably hydroxypropyl methylcellulose, and 11-[4-[2-(2-hydroxyethoxy)ethyl]-1piperazinyv]dibenzo-[b,f][1,4] thiazepine, or a pharmaceutically acceptable salt thereof, together with one or more pharmaceutically acceptable excipients.

The term gelling agent as used herein means any substance, particularly a hydrophilic substance, which forms a gel when in contact with water and thus includes such substances as hydroxypropyl methylcellulose, hydroxypropylcellulose, hydroxymethylcellulose, hydroxyethylcellulose, hydroxypropyl ethylcellulose, methylcellulose, ethylcellulose, carboxyethylcellulose, carboxymethyl hydroxyethylcellulose, carbomer, sodium carboxymethylcellulose, polyvinylpyrrolidone, and the like, or mixtures thereof. The gelling agent is preferably hydroxypropyl methylcellulose.

The amount of gelling agent, preferably hydroxypropyl methylcellulose, is preferably selected such that the active ingredient is released from the formulation, in a controlled fashion, over a period of 4 hours or longer, preferably over a period of 8 hours or longer and in particular over a period of between 8 and 24 hours, that is so that at least 60% of the active ingredient has been released at the end of this period.

The gelling agent, preferably hydroxypropyl methylcellulose, is conveniently present in about 5 to 50% (by weight), more conveniently about 5 to 40%, most conveniently about 8 to 35% and in particular about 10 to 35%. It is generally preferred that the gelling agent, preferably hydroxypropyl methylcellulose, is present in about 10 to 30%, more preferably about 15 to 30%.

The hydroxypropyl methylcellulose may contain more than one grade of polymer and is commercially available under several trademarks, e.g. METHOCEL® E, F, J and K from the Dow Chemical Company, U.S.A. and METALOSE™ SH from Shin-Etsu, Ltd., Japan. The various grades available under a given trademark represent differences in methoxy and hydroxypropoxy content as well as in viscosity. The methoxy content ranges from 16.5 to 30% by weight, the hydroxypropoxy content ranges from 4 to 32% by weight and the viscosities of a 2% aqueous solution at 20° C. range from 3 cps to 100,000 cps. For example, the hydroxypropyl methylcellulose preferably comprises (a) a polymer with a viscosity of about 40 to 60 cps (in particular about 50 cps), a methoxy content of about 28 to 30% by weight and a hydroxypropoxy content of from about 7 to less than 9% by weight; or (b) a polymer with a viscosity of about 3,500 to 5,600 cps (in particular about 4,000 cps), a methoxy content of about 28 to 30% by weight and a hydroxypropoxy content of about 7 to 12% by weight; or (c) a polymer with a viscosity of about 80 to 120 cps (in particular about 100 cps), a methoxy content of about 19 to 24% by weight and a hydroxypropoxy content of from about 7 to less than 9% by weight; or (d) a polymer with a viscosity of about 3500 to 5600 cps (in particular about 4,000 cps), a methoxy content of about 19 to 24% by weight and a hydroxypropoxy content of about 7 to 12% by weight, or mixtures thereof. More preferably, the hydroxypropyl methylcellulose is selected from the group consisting of (a)–(d) or mixtures thereof as described above with the proviso that if the formulation contains a hydroxypropyl methylcellulose described under (d) above the total amount of hydroxypropyl methylcellulose present in the formulation must be greater than 25.8% by weight.

In one embodiment the hydroxypropyl methylcellulose comprises 8 to 12% of a polymer having a viscosity of about 4,000 cps, and preferably about 5 to 10%. In a further embodiment hydroxypropyl methylcellulose comprises 10 to 35% of a polymer having a viscosity of about 50 cps, and preferably about 10 to 15%.

In a specific embodiment the hydroxypropyl methylcellulose comprises 15% of a polymer having a viscosity of about 50 cps, and optionally about 5% of a hydroxypropyl methylcellulose polymer having a viscosity of about 4,000 cps.

In particular the 11-[4-[2-(2-hydroxyethoxy)-ethyl]-1-piperazinyl]dibenzo-[b,f][1,4]thiazepine, or pharmaceutically acceptable salt thereof (preferably the hemifumarate salt),. is present in about 10 to 90% by weight, preferably about 20 to 80% by weight, more preferably about 35 to 65% by weight, most preferably about 40 to 60% by weight and especially about 43.2 to 57.6% by weight.

The formulation will, in general, contain one or more excipients. Such excipients will include diluents such as lactose, microcrystalline cellulose, dextrose, mannitol, sucrose, sorbitol, gelatin, acacia, dicalcium phosphate, tricalcium phosphate, monocalcium phosphate, sodium phosphate, sodium carbonate and the like, preferably lactose and microcrystalline cellulose; lubricants such as stearic acid, zinc, calcium or magnesium stearate and the like, preferably magnesium stearate; binders such as sucrose, polyethylene glycol, povidone (polyvinylpyrrolidone), corn or maize starch, pregelatinized starch and the like, preferably povidone (polyvinylpyrrolidone); colorants such as ferric oxides, FD & C dyes, lakes and the like; flavoring agents; and pH modifiers which include suitable organic acids or alkali metal (e.g. lithium, sodium or potassium) salts thereof, such as benzoic acid, citric acid, tartaric acid, succinic acid, adipic acid and the like or the corresponding alkali metal salts thereof, preferably the alkali metal salts of such acids and in particular the sodium salt of citric acid (i.e. sodium citrate). The excipient(s) will, in general, be present in about 10 to 90% by weight, preferably about 20 to 80% by weight, more preferably about 20 to 45% by weight, most preferably about 20 to 40% by weight and especially about 22.4 to 36.8% by weight. The formulation preferably may contain one or more pharmaceutically acceptable excipients selected from the group consisting of microcrystalline cellulose, lactose, magnesium stearate, sodium citrate and povidone. In particular, the formulation may contain one or more of (a) microcrystalline cellulose, preferably in the amount of about 4 to 20% by weight, (b) lactose, preferably in the amount of about 5 to 20% by weight, (c) magnesium stearate, preferably in the amount of about 1 to 3% by weight, (d) about 10 to 30% by weight, preferably about 12.5 to 25% and in particular about 12.5% by weight of sodium citrate, and (e) about 1 to 15% by weight, preferably about 4 to 6% by weight and in particular about 5% by weight of povidone (polyvinylpyrrolidone).

According to the present invention there is also provided a sustained release formulation comprising a gelling agent, preferably hydroxypropyl methylcellulose, and 11-[-4-[2-(2-hydroxyethoxy)ethyl]-1-piperazinyl]dibenzo-[b,f][1,4]thiazepine, or a pharmaceutically acceptable salt thereof, together with one or more pharmaceutically acceptable excipients wherein one of the excipients is a pH modifier.

According to the present invention there is also provided a sustained release formulation comprising 11 -[4-[2-(2-hydroxyethoxy)ethyl]- 1 -piperazinyl] dibenzo-[b,f][1,4] thiazepine, or a pharmaceutically acceptable salt thereof, as active ingredient and 5 to 40% of hydroxypropyl methylcellulose, together with one or more pharmaceutically acceptable excipients.

According to the present invention there is also provided a sustained release formulation comprising about 35 to 65% of 11-[4-[2-(2-hydroxyethoxy)ethyl]-1-piperazinyl]dibenzo[b,f][1,4]thiazepine, or a pharmaceutically acceptable salt thereof, as active ingredient and about 5 to 40% by weight of hydroxypropyl methylcellulose, together with one or more pharmaceutically acceptable excipients.

According to the present invention there is also provided a sustained release formulation comprising about 35 to 65% of 11-[4-[2-(2-hydroxyethoxy)ethyl]-1-piperazinyl]dibenzo[b,f][1,4]thiazepine, or a pharmaceutically acceptable salt thereof, as active ingredient and about 15 to 30% of hydroxypropyl methylcellulose, together with about 20 to 45% of one or more pharmaceutically acceptable excipients.

According to the present invention there is also provided a sustained release formulation comprising about 35 to 65% of 11-[4-[2-(2-hydroxyethoxy)ethyl]-1 1-piperazinyl]-dibenzo[b,f][1,4]thiazepine as active ingredient, or a pharmaceutically acceptable salt thereof, about 5 to 40% by weight of hydroxypropyl methylcellulose, about 4 to 12% microcrystalline cellulose, about 8 to 20% lactose and the remainder being one or more further pharmaceutically acceptable excipients. Such further excipients may include components which act as a lubricant (for example, magnesium stearate) during the manufacture of the formulation or dosage form.

According to the present invention there is also provided a sustained release formulation comprising about 5 to 40% by weight of a hydroxypropyl methylcellulose selected from the group consisting of (a) a hydroxypropyl methylcellulose having a viscosity of about 40 to 60 cps, a methoxy content of about 28 to 30% by weight and a hydroxypropoxy content of from about 7 to less than 9% by weight, (b) a hydroxypropyl methylcellulose having a viscosity of about 3,500 to 5,600 cps, a methoxy content of about 28 to 30% by weight and a hydroxypropoxy content of about 7 to 12% by weight, (c) a hydroxypropyl methylcellulose having a viscosity of about 80 to 120 cps, a methoxy content of about 19 to 24% by weight and a hydroxypropoxy content of from about 7 to less than 9% by weight and (d) a hydroxypropyl methylcellulose having a viscosity of about 3,500 to 5,600 cps, a methoxy content of about 19 to 24% by weight and a hydroxypropoxy content of about 7 to 12% by weight, or mixtures thereof; about 35 to 65% by weight of 11-[4[2-(2-hydroxyethoxy)ethyl]-1-piperazinyl) -dibenzo[b,f][1,4]thiazepine or a pharmaceutically acceptable salt thereof; and about 20 to 45% by weight of one or more pharmaceutically acceptable excipients; with the proviso that if the formulation contains a hydroxypropyl methylcellulose described under (d) above the total amount of hydroxypropyl methylcellulose present in the formulation must be greater than 25.8% by weight.

Other formulations within the ambit of this latter group are those comprising about 8 to 35% by weight of a hydroxypropyl methylcellulose selected from the group consisting of (a) a hydroxypropyl methylcellulose having a viscosity of about 40–60 cps, a methoxy content of about 28 to 30% by weight and a hydroxypropoxy content of about 7 to less than 9% by weight, (b) a hydroxypropyl methylcellulose having a viscosity of about 3,500 to 5,600 cps, a methoxy content of about 28 to 30% by weight and a hydroxypropoxy content of about 7 to 12% by weight, (c) a hydroxypropyl methylcellulose having a viscosity of about 80 to 120 cps, a methoxy content of about 19 to 24% by weight and a hydroxypropoxy content of about 7 to less than 9% by weight and (d) a hydroxypropyl methylcellulose having a viscosity of about 3,500 to 5,600 cps, a methoxy content of about 19 to 24% by weight and a hydroxypropoxy content of about 7 to 12% by weight or mixtures thereof; about 35 to 65% by weight of 11-[4-[2-(2-hydroxyethoxy)ethyl]1-piperazinyl]dibenzo[b,f][1,4]thiazepine or a pharmaceutically acceptable salt thereof; and about 20 to 45% by weight of one or more pharmaceutically acceptable excipients.

Still other formulations within the ambit of this latter group are those comprising about 10 to 30% by weight of a hydroxypropyl methylcellulose selected from the groups (a)–(d) or mixtures thereof as described above; about 40 to 60% by weight of 11 -[4-[2-(2-hydroxyethoxy)ethyl]-1-piperazinyl]dibenzo[b,f] [1,4]thiazepine or a pharmaceutically acceptable salt thereof; and about 20 to 40% by weight of one or more pharmaceutically acceptable excipients.

Preferred formulations within this latter group are those comprising about 15 to 30% by weight of a hydroxypropyl methylcellulose selected from the groups (a)–(d) or mixtures thereof as described above; about 43.2 to 57.6% by weight of 11-[4-[2-(2-hydroxyethoxy)ethyl]-1-piperazinyl]dibenzo[b,f][1,4]thiazepine or a pharmaceutically acceptable salt thereof; and about 22.4 to 36.8% by weight of one or more pharmaceutically acceptable excipients.

Particularly preferred formulations within this latter group are those comprising about 15 to 30% by weight of a hydroxypropyl methylcellulose selected from the groups (a)–(d) or mixtures thereof as described above; about 43.2 to 57.6% by weight of 11-[4-[2-(2-hydroxyethoxy)ethyl]-1-piperazinyl]dibenzo[b,f]-[1,4]thiazepine or a pharmaceutically acceptable salt thereof; and about 22.4 to 36.8% by weight of one or more pharmaceutically acceptable excipients selected from the group consisting of (a) about 4 to 12% by weight of microcrystalline cellulose, (b) about 5 to 20% by weight of lactose, (c) about 1 to 3% by weight of magnesium stearate, (d) about 10 to 30% by weight of sodium citrate and (e) about 1 to 15% by weight of povidone (polyvinylpyrrolidone).

In the above-described formulations the 11-[4-[2-(2-hydroxyethoxy)ethyl]-1-piperazinyl]dibenzo[b,f][1,4]-thiazepine is preferably in the form of a hemifumarate salt which form has an equilibrium solubility in water at 20° C. of 3.29 mg/mL.

Formulations of particular interest include those described in the accompanying Examples and so formulations substantially as defined in the accompanying Examples are provided as a further feature of the present invention.

As mentioned above, the compound 11-[4-[2-(2-hydroxyethoxy)ethyl]-1-piperazinyl]dibenzo[b,f]]1,4]-thiazepine, and its pharmaceutically acceptable salts, exhibit useful antidopaminergic activity and may be used, for example, as an antipsychotic agent (for example, for the management of the manifestations of psychotic disorders) or as a treatment for hyperactivity. Thus, the present invention also provides a method of treating psychotic states, for example psychosis, in a warm-blooded animal, such as man, which comprises administering an effective amount of the formulation of the present invention to said warm-blooded animal.

The present invention also provides a method of treating hyperactivity in a warm-blooded animal which comprises administering to said warm-blooded animal an effective amount of a formulation of the present invention.

The formulations of the present invention may be prepared by conventional technology well known to those skilled in the art such as wet granulation, direct compression, dry compaction (slugging) and the like. Thus, for example, the active ingredient 11-[4-[2-(2-hydroxyethoxy)ethyl]-1-piperazinyl]-dibenzo[b,f]-[1,4]thiazepine, or a pharmaceutically acceptable salt thereof, a gelling agent, preferably hydroxypropyl methylcellulose, and other excipients are mixed together to form the sustained release formulations of the present invention. Preferably the active ingredient 11-[4-[2-(2-hydroxyethoxy)ethyl]-1-piperazinyl]dibenzo[b,f][1,4]thiazepine, or a pharmaceutically acceptable salt thereof, a gelling agent, preferably hydroxypropyl methylcellulose, and other excipients are mixed together to form a mixture suitable for compressing into tablets, which mixture is then compressed to form tablets or is filled into capsules.

The mixing process is preferably carried out by mixing the components, wet granulating the mixed components, drying the mixture, milling the dried mixture, blending the mixture with a lubricant such as magnesium stearate and compressing the blended mixture to form tablets or filling the blended mixture into capsules.

A preferred process for preparing the formulations of the invention comprises the following steps:

(a) mixing 11-[4-[2-(2-hydroxyethoxy)ethyl]1-piperazinyl]dibenzo[b,f][1,4]-thiazepine, or a pharmaceutically acceptable salt thereof, a gelling agent, preferably hydroxypropyl methylcellulose, and other excipients;

(b) wet granulating the mixed components;

(c) drying the mixture;

(d) milling the dried mixture;

(e) blending the mixture with a lubricant such as magnesium stearate; and (f) compressing the blended mixture to form tablets.

The dosage forms may be coated with one or more coatings as is well known in the art such as, for example, shellac, zein, hydroxypropyl cellulose, hydroxypropyl methylcellulose, ethyl cellulose, polymethacrylates, polyvinyl acetate phthalate, cellulose acetate phthalate, triacetin, dibutyl sebacate, a mixture of polyethylene glycol, titanium dioxide and hydroxypropyl methylcellulose, and the like.

The sustained release properties of the formulation of the present invention may be demonstrated by monitoring the dissolution of the active ingredient. The dissolution of the active ingredient may be monitored using standard procedures well known to those skilled in the art (e.g. the dissolution test procedures, such as the Rotating Basket Method (Apparatus I) or Paddle Method (Apparatus II), disclosed in the U.S. Pharmacopeia (USP)). Such procedures include those in which the formulation is immersed in an aqueous medium such as water or hydrochloric acid and aliquots of the medium are withdrawn at various time points over a period of 24 hours. The aliquots are analyzed using high pressure liquid chromatography (HPLC) with UV detection to determine the concentration of dissolved active ingredient using standard methodology. In a particular example a tablet is immersed in about 900 mL of water and the dissolution profile determined. In another particular example, the dissolution profile is determined by the Rotating Basket method by immersing a tablet in 750 mL of 0.1N HCl for 2 hours at a speed of 100 rpm and then adding 250 mL of 0.2 M phosphate buffer to the dissolution media to afford a pH of 6.2.

The formulation preferably releases the active ingredient in a controlled manner over a period of up to about 8 hours or longer. For example, the formulation described in Example 2 below released about 90% of the active ingredient over 16 hours, and the formulation described in Example 1 released about 90% of the active ingredient over a period of 8 hours.

Figure 2:
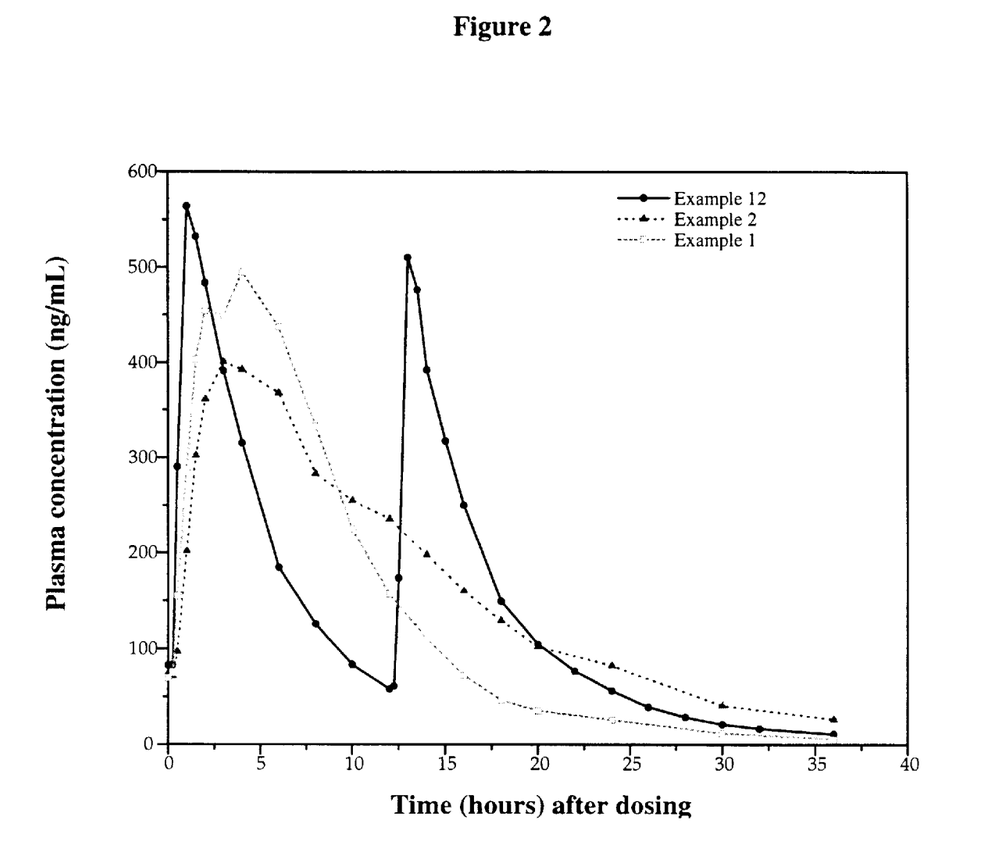
FIG. 2 shows the plasma concentration versus time profiles of the active ingredient for the sustained release formulations of examples 1 and 2 and the immediate release formulation of example 12.

The plasma concentration versus time profiles of the active ingredient illustrated in FIG. 2 were obtained utilizing the following procedure. Thirty-two patients were assigned to either Group A or Group B with 16 patients in each group. After a 2-day drug-free period (days 1 and 2), all patients were given oral doses of the immediate release formulation of example 12 twice daily for a 9-day period (days 3 through 11) with fixed step-wise increases in dose from 25 to 200 mg. Starting on day 12, patients began a randomized treatment sequence within their respective groups (Group A or B). Group A patients followed a treatment sequence that included one of each of the following formulations of the active ingredient administered according to the sequence randomized: two 100 mg tablets of the immediate release formulation of example 12 while fasting administered every 12 hours (Treatment 1), one 400 mg tablet of the formulation of example 2 while fasting (Treatment 2) and one 400 mg tablet of the formulation of example 2 with a meal (Treatment 3). Group B patients were randomized to a treatment sequence that included one of each of the following formulations of the active ingredient administered according to the sequence randomized: two 100 mg tablets of the immediate release formulation of example 12 while fasting administered every 12 hours (Treatment 1), one 400 mg tablet of the formulation of example 1 while fasting (Treatment 4) and one 400 mg tablet of the formulation of example 1 with a meal (Treatment 5). On days 12, 16 and 20 patients received trial treatment according to their assigned treatment sequences. On the evenings of days 13 and 17, patients received 200 mg doses of the immediate release formulation of example 12 and on days 14, 15, 18 and 19 the patients received 200 mg dose of the immediate release formulation of example 12 twice daily. Blood samples were taken from each subject on days 3, 10, 11, 14, 15, 18 and 19 before the morning dose. On days, 12, 16 and 20 blood samples were taken from each subject immediately before dose administration and at specified time intervals from immediately after dose administration to 36 hours after dose administration. The concentration of the active ingredient in the blood samples was quantified using liquid-liquid extraction and high performance liquid chromatography with ultraviolet absorbance detection. The plasma concentration of the active ingredient over time profiles for the formulations of examples 1 (n=11), 2(n=10) and 12(n=10 for Group A and 12 for Group B) are illustrated in FIG. 2 and Table A summarizes the mean area under the curve (AUC) values for a 24 hour dosing interval and the mean maximum blood concentration ($C_{max}$) values for each of the examples.

TABLE A

| Example No. | Group A | | Group B | |
| --- | --- | --- | --- | --- |
| | $AUC_{0-24}$ | $C_{max}$ | $AUC_{0-24}$ | $C_{max}$ |
| 1 | — | — | 4886 | 565 |
| 2 | 5609 | 433 | — | — |
| 12 | 5347 | 703 | 4818 | 563 |

The dose of the compound of the present invention which is administered will necessarily be varied according to principles well known in the art taking account of the route of administration, the duration of treatment, the severity of the psychotic condition, the size and age of the patient, the potency of the active component and the patient's response thereto. An effective dosage amount of the active component can thus readily be determined by the clinician after a consideration of all criteria and using his best judgment on the patient's behalf. In general, the compound will be administered to a warm blooded animal (such as man) so that an effective dose is received, generally a daily dose in the range of about 0.01 to about 40 mg/kg body weight. For example, when administered orally, it is generally administered in the range of about 0.1 to about 40 mg/kg body weight. Preferably, the compound of the present invention is administered in about a 25, 50, 200, 300 or 400 mg strength.

The formulation of the present invention will, in general, be in the form of a unit dosage form, and, in particular, the formulation will be in the form of a tablet.

It will be apparent to those skilled in the art that the formulation can be co-administered with other therapeutic or prophylactic agents and/or medicaments that are not medically incompatible therewith. The formulation of the present invention does not, in general, show any indication of overt toxicity in laboratory test animals at several multiples of the minimum effective dose of the active ingredient.

The invention is further illustrated by the following non-limiting Examples in which temperatures are expressed in degrees Celsius. The compound 11-[4-[2-(2-hydroxyethoxy)ethyl]-1-piperazinyl]dibenzo[b,f]]1,4]-thiazepine, and its pharmaceutically acceptable salts, may be prepared as described in published European Patents EP 240,228 or 282,236 as well as in U.S. Pat. No. 4,879,288, the entire contents of which are herein incorporated by reference.

EXAMPLE 1

The following process was used to prepare tablets having the composition defined in Table 1.

11-[4-[2-(2-hydroxyethoxy)ethyl]-1-piperazinyl]-dibenzo-[b,f]][1,4]thiazepine hemifumurate (3453.8g), lactose (1144.7g), microcrystalline cellulose (381.5g) and METHOCEL® E50LV (900 g) were blended in a planetary mixer for approximately 3 minutes.

The mixture was wet granulated in a planetary mixer using purified water. The wet mass was dried in a fluidized bed drier at about 65° C. until the loss on drying was less than about 3% as measured by a moisture balance.

The dried granulation was milled using a hammer type or similar mill operating at fast speed, knives forward with suitable screen (e.g. 20 to 40 mesh).

Magnesium stearate was passed through an appropriate screen (e.g. 20 to 40 mesh).

The dry granulated material was blended for approximately 3 minutes in a conventional blender (for example, Patterson-Kelley Twin Shell) with the screened magnesium stearate.

The blended mixture was compressed into tablets using a conventional rotary tablet press (for example, Kilian LX-21).

TABLE 1

|  | mg/Tablet | % of Tablet |
| --- | --- | --- |
| Active ingredient (a) | 460.51 | 57.6 |
| Lactose NF | 152.62 | 19.1 |
| Microcrystalline Cellulose NF | 50.87 | 6.3 |
| METHOCEL ® E50LV Premium (b) | 120.00 | 15.0 |
| Purified water (c) | q.s | — |
| Magnesium stearate NF | 16.00 | 2.0 |

(a) The active ingredient is 11-[4-[2-(2-hydroxyethoxy)ethyl]-1-piperazinyl]-dibenzo[b,f][1,4]thiazepine hemifumarate
(b) METHOCEL ® E50LV Premium is hydroxypropyl methylcellulose with a viscosity of 40–60 cps, a methoxy content of 28 to 30% by weight and a hydroxypropoxy content of 7 to 12% by weight which may be obtained from The Dow Chemical Company, Michigan, USA. This product meets the specifications for HPMC 2910 USP. Note that the particular METHOCEL ® E50LV Premium utilized in this example had a viscosity of 48 cps, a methoxy content of 28.9% by weight and a hydroxypropoxy content of less than 9.0% by weight (i.e. 8.0%).
(c) Added but not retained.

The plasma concentration over time profile of the active ingredient for the formulation of Example 1 is shown in FIG. 2.

EXAMPLE 2

The procedure described in Example 1 was repeated using METHOCEL® E50LV and METHOCEL® E4M in place of METHOCEL® E50LV to afford tablets of the following composition.

TABLE 2

|  | mg\Tablet | % of Tablet |
| --- | --- | --- |
| Active ingredient (a) | 460.51 | 57.6 |
| Lactose NF | 81.74 | 10.2 |
| Microcrystalline Cellulose NF | 81.75 | 10.2 |
| METHOCEL ® E50LV Premium (b) | 120.00 | 15.0 |
| METHOCEL ® E4M Premium CR (d) | 40.00 | 5.0 |

TABLE 2-continued

|  | mg\Tablet | % of Tablet |
| --- | --- | --- |
| Purified water (c) | q.s | — |
| Magnesium stearate NF | 16.00 | 2.0 |

(a) The active ingredient is 11-[4-[2-(2-hydroxyethoxy)ethyl]-1-piperazinyl]-dibenzo[b,f][1,4]thiazepine hemifumarate
(b) METHOCEL ® E50LV Premium is hydroxypropyl methylcellulose with a viscosity of 40–60 cps, a methoxy content of 28 to 30% by weight and a hydroxypropoxy content of 7 to 12% by weight which may be obtained from The Dow Chemical Company, Michigan, USA. This product meets the specifications for HPMC 2910 USP. Note that the particular METHOCEL ® E50LV Premium utilized in this example had a viscosity of 48 cps, a methoxy content of 28.9% by weight and a hydroxypropoxy content of less than 9.0% by weight (i.e. 8.0%).
(c) Added but not retained.
(d) METHOCEL ® E4M Premium CR is hydroxypropyl methylcellulose with a viscosity of 3,500 to 5,600 cps, a methoxy content of 28 to 30% by weight and a hydroxypropoxy content of 7 to 12% by weight which may be obtained from The Dow Chemical Company, Michigan, USA. This product meets the specifications from HPMC 2910 USP. Note that the particular METHOCEL ® E4M Premium CR utilized in this example had a viscosity of 4364 cps, a methoxy content of 28.5% by weight and a hydroxypropoxy-content of 7.8% by weight.

The plasma concentration over time profile of the active ingredient for the formulation of Example 2 is shown in FIG. 2.

EXAMPLE 3

Following a procedure similar to that described in Example 1, tablets of the following composition can be prepared.

TABLE 3

|  | mg\Tablet | % of Tablet |
| --- | --- | --- |
| Active ingredient (a) | 345.38 | 43.2 |
| Lactose NF | 49.31 | 6.2 |
| Microcrystalline Cellulose NF | 49.31 | 6.2 |
| Sodium citrate | 100.00 | 12.5 |
| METHOCEL ® K100LV Premium CR (b) | 200.00 | 25.0 |
| METHOCEL ® K4M Premium CR (c) | 40.00 | 5.0 |
| Purified water (d) | q.s | — |
| Magnesium stearate NF | 16.00 | 2.0 |

(a) The active ingredient is 11-[4-[2-(2-hydroxyethoxy)ethyl]-1-piperazinyl] dibenzo[b,f][1,4]thiazepine hemifumarate
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in this example must have a hydroxypropoxy content of less than 9.0% by weight.
(c) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% be weight which may be obtained from The Dow Chemical Company, Michigan, USA. This product meets the specification of HPMC 2208 USP.
(d) Added but not retained

EXAMPLE 4

Following a procedure similar to that described in Example 1, tablets of the following composition can be prepared.

TABLE 4

|  | mg\Tablet | % of Tablet |
|---|---|---|
| Active ingredient (a) | 345.38 | 43.2 |
| Lactose NF | 89.31 | 11.1 |
| Microcrystalline Cellulose NF | 89.31 | 11.1 |
| Sodium citrate | 100.00 | 12.5 |
| METHOCEL ® K100LV Premium CR (b) | 120.0 | 15.0 |
| METHOCEL ® E4M Premium CR (c) | 40.00 | 5.0 |
| Purified water (d) | q.s. | — |
| Magnesium stearate NF | 16.00 | 2.0 |

(a) The active ingredient is 11-[4-[2-(2-hydroxyethoxy)ethyl]-1-piperazinyl]dibenzo[b,f][1,4]thiazepine hemifumarate
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in this example must have a hydroxypropoxy content of less than 9.0% by weight.
(c) METHOCEL ® E4M Premium CR is hydroxypropyl methylcellulose with a viscosity of 3,500 to 5,600 cps, a methoxy content of 28 to 30% by weight and a hydroxypropoxy content of 7 to 12% by weight which may be obtained from the Dow Chemical Company, Michigan, USA. This product meets the specification of HPMC 2910 USP.
(d) Added but not retained

EXAMPLE 5

Following a procedure similar to that described in Example 1, tablets of the following composition can be prepared.

TABLE 5

|  | mg\Tablet | % of Tablet |
|---|---|---|
| Active ingredient (a) | 345.38 | 43.2 |
| Lactose NF | 69.31 | 8.7 |
| Microcrystalline Cellulose NF | 69.31 | 8.7 |
| Sodium citrate | 100.00 | 12.5 |
| METHOCEL ® K100LV Premium CR (b) | 200.00 | 25.0 |
| Purified water (d) | q.s. | — |
| Magnesium stearate NF | 16.00 | 2.0 |

(a) The active ingredient is 11-[4-[2-(2-hydroxyethoxy)ethyl]-1-piperazinyl]dibenzo[b,f][1,4]thiazepine hemifumarate
(b) METHOCEL ® K100LV Premium CR is hydroxypropyl methylcellulose with a viscosity of 80 to 120 cps, a methoxy content of 19 to 24% by weight and a hydropropoxy content of 7 to 12% by weight which may be obtained from The Dow Chemical Company, Michigan, USA. This product meets the specifications for HPMC 2208 USP. Note that the particular METHOCEL ® K100LV Premium CR utilized in this example must have a hydroxypropoxy content of less than 9.0% by weight.
(c) Added but not retained.

EXAMPLE 6

Following a procedure similar to that described in Example 1, tablets of the following composition can be prepared.

TABLE 6

|  | mg\Tablet | % of Tablet |
|---|---|---|
| Active ingredient (a) | 345.38 | 43.2 |
| Povidone USP (b) | 40.00 | 5.0 |
| Microcrystalline Cellulose NF | 38.62 | 4.8 |
| Sodium citrate | 200.00 | 25.0 |
| METHOCEL ® E50LV Premium (c) | 80.00 | 10.0 |
| METHOCEL ® E4M Premium CR (d) | 80.00 | 10.0 |
| Purified water (e) | q.s | — |
| Magnesium stearate NF | 16.00 | 2.0 |

(a) The active ingredient is 11-[4-[2-(2-hydroxyethoxy)ethyl]-1-piperazinyl]dibenzo[b,f][1,4]thiazepine hemifumarate
(b) The reagent is a polyvinylpyrrolidone polymer having a K-value of 29–32 which may be obtained from ISP Technologies Inc., Wayne, New Jersey, USA, under the trademark PLASDONE ® K-29/32. This product meets the specifications for Povidone USP.
(c) METHOCEL ® E50LV Premium is hydroxypropyl methylcellulose with a viscosity of 40–60 cps, a methoxy content of 28 to 30% by weight and a hydroxypropoxy content of 7 to 12% by weight which may be obtained from The Dow Chemical Company, Michigan, USA. This product meets the specifications for HPMC 2910 USP. Note that the particular METHOCEL ® E50LV Premium utilized in this example must have a hydroxypropoxy content of less than 9.0% by weight.
(d) METHOCEL ® E4M Premium CR is hydroxypropyl methylcellulose with a viscosity of 3,500 to 5,600 cps, a methoxy content of 28 to 30% by weight and a hydroxypropoxy content of 7 to 12% by weight which may be obtained from The Dow Chemical Company, Michigan, USA. This product meets the specifications for HPMC 2910 USP.
(e) Added but not retained

EXAMPLE 7

Following a procedure similar to that described in Example 1, tablets of the following composition can be prepared.

TABLE 7

|  | mg\Tablet | % of Tablet |
|---|---|---|
| Active ingredient (a) | 345.38 | 43.2 |
| Povidone USP (b) | 40.00 | 5.0 |
| Microcrystalline Cellulose NF | 38.62 | 4.8 |
| Sodium citrate | 200.00 | 25.0 |
| METHOCEL ® E50LV Premium (c) | 80.00 | 10.0 |
| METHOCEL ® E4M Premium CR (d) | 80.00 | 10.0 |
| Purified water (e) | q.s | — |
| Magnesium stearate NF | 16.00 | 2.0 |

(a) The active ingredient is 11-[4-[2-(2-hydroxyethoxy)ethyl]-1-piperazinyl]dibenzo[b,f][1,4]thiazepine hemifumarate.
(b) This reagent is a polyvinylpyrrolidone polymer having a K-value of 90 which may be octained from ISP Technologies Inc., Wayne, New Jersey, USA, inder the trademark PLASDONE ® K-90. This product meets the specifications for Povidone USP.
(c) METHOCEL ® E50LV Premium is hydroxypropyl methylcellulose with a viscosity of 40–60 cps, a methoxy content of 28 to 30% by weight and a hydroxypropoxy content of 7 to 12% by weight which may be obtained from The Dow Chemical Company, Michigan, USA. This product meets the specifications for HPMC 2910 USP. Note that the particular METHOCEL ® E50LV Premium utilized in this example must have a hydroxypropoxy content of less than 9.0% by weight.
(d) METHOCEL ® E4M Premium CR is hydroxypropyl methylcellulose with a viscosity of 3,500 to 5,600 cps, a methoxy content of 28 to 30% by weight and a hydroxypropoxy content of 7 to 12% by weight which may be obtained from The Dow Chemical Company, Michigan, USA. This product meets the specifications for HPMC 2910 USP.
(e) Added but not retained.

Following a procedure similar to that described in Example 1, tablets of the following compositions were prepared:

TABLE 8

|  | Example 8 | | Example 9 | | Example 10 | |
| --- | --- | --- | --- | --- | --- | --- |
|  | mg/tablet | % of tablet | mg/tablet | % of tablet | mg/tablet | % of tablet |
| Active Ingredient (a) | 345.38 | 43.2 | 345.38 | 43.2 | 345.38 | 43.2 |
| Lactose NF | 109.31 | 13.7 | 69.31 | 8.7 | 49.31 | 6.2 |
| Microcrystalline Cellulose NF | 109.31 | 13.7 | 69.31 | 8.7 | 49.31 | 6.2 |
| Sodium citrate | 100.00 | 12.5 | 100.00 | 12.5 | 100.00 | 12.5 |
| METHOCEL ® K100LV Premium CR (b) | 120.00 | 15.0 | 200.00 | 25.0 | 200.00 | 25.0 |
| METHOCEL ® K4M Premium CR (c) | — | — | — | — | 40.00 | 5.0 |
| Purified water (d) | q.s. | — | q.s. | — | q.s. | — |
| Magnesium stearate NF | 16.00 | 2.0 | 16.00 | 2.0 | 16.00 | 2.0 |

(a) The active ingredient is 11-[4-[2-(2-hydroxyethoxy)ethyl]-1-piperazinyl]-dibenzo[b,f][1,4]thiazepine hemifumarate
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in this example had a viscosity of 90 cps, a methoxy content of 22.7% by weight and a hydroxypropoxy contentof 8.5% by weight.
(c) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% by weight, which may be obtained from the Dow Chemical Company, Michigan, USA. This product meets the specification of HPMC 2208 USP. Note that the particular METHOCEL ® K4M Premium CR utilized in this example had a viscosity of 4105 cps, a methoxy content of 22.3% by weight and a hydroxypropoxy content of 9.7% by weight.
(d) Added but not retained.

Figure 1:
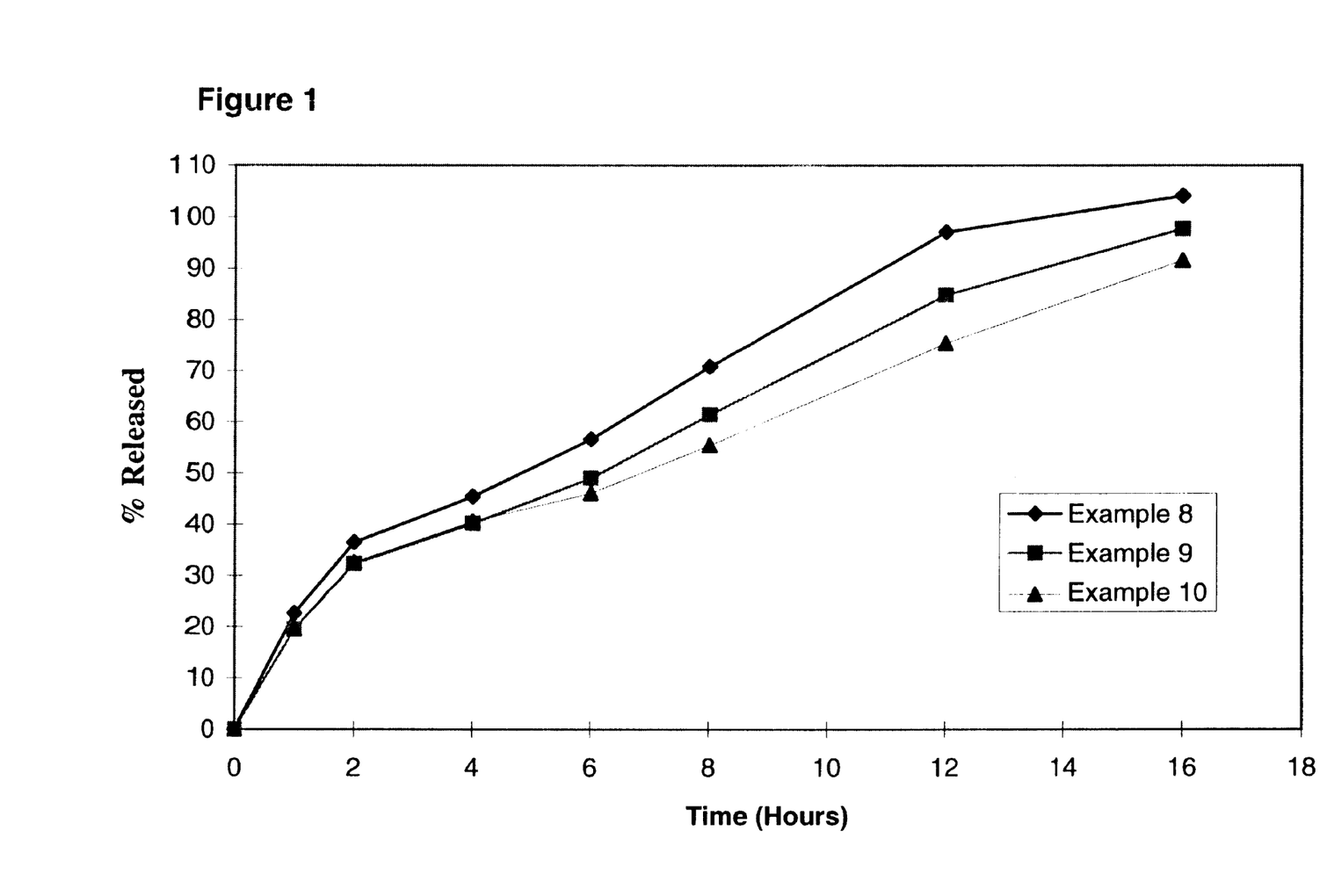
FIG. 1 shows the release (dissolution) profiles of the sustained release formulations of Examples 8, 9 and 10 which are obtained by immersing a suitable tablet in 750 mL of 0.1 N HCl for 2 hours at 37° C. and a speed of 100 rpm and then adding 250 mL of 0.2 M sodium phosphate buffer to the dissolution media to afford a pH of 6.2.

The release dissolution profile of the formulations of Examples 8, 9 and 10 are shown in FIG. 1.

EXAMPLE 11

Following a procedure similar to that described in Example 1, tablets of the following composition were prepared:

|  | mg/Tablet | % of Tablet |
| --- | --- | --- |
| Active ingredient (a) | 345.38 | 43.2 |
| Povidone USP (b) | 80.00 | 10.00 |
| Sodium citrate USP | 100.00 | 12.5 |
| Microcrystalline cellulose NF | 138.62 | 17.3 |
| METHOCEL ® E4M Premium CR (c) | 120.00 | 15.0 |
| Purified water (d) | q.s. | — |
| Magnesium Stearate NF | 16.0 | 2.0 |

(a) The active ingredient is 11-[4-[2(2-hydroxyethoxy)ethyl]-1-piperazinyl]-dibenzo[b,f][1,4]thiazepine hemifumarate
(b) This reagent is a polyvinylpyrrolidone polymer having a K-value of 90 which may be obtained from ISP Technologies Inc., Wayne, New Jersey, USA, under the trademark PLASDONE ® K-90. This product meets the specifications for Povidone USP.
(c) METHOCEL ® E4M Premium CR is hydroxypropyl methylcellulose with a viscosity of 3,500 to 5,600 cps, a methoxy content of 28 to 30% by weight and a hydroxypropoxy content of 7 to 12% by weight which may be obtained from The Dow Chemical Company, Michigan, USA. This product meets the specifications for HPMC 2910 USP. Note that the particular METHOCEL ® E4M Premium CR utilized in this example had a viscosity of 4364 cps, a methoxy content of 28.5% by weight and a hydroxypropoxy-content of 7.8% by weight.
(d) Added by not retained.

EXAMPLE 12

|  | Mg/Tablet |
| --- | --- |
| CORE | |
| Active ingredient (a) | 115.13 |
| Povidone USP (b) | 8.33 |
| Dicalcium phosphate dihydrate USP | 10.00 |
| Microcrystalline cellulose NF | 32.88 |
| Sodium starch glycolate NF | 8.33 |
| Lactose NF | 22.33 |
| Magnesium stearate NF | 3.00 |
| Purified water (c) | q.s. |
| COATING | |
| Hydroxypropyl methylcellulose 2910 USP (d) | 5.00 |
| Polyethylene glycol 400 NF | 1.00 |
| Yellow ferric oxide NF | 0.15 |
| Titanium dioxide USP | 1.85 |

(a) The active ingredient is 11-[4-[2-(2-hydroxyethoxy)ethyl]-1-piperazinyl] dibenzo[b,f][1,4]thiazepine hemifumarate.
(b) This reagent is a polyvinylpyrrolidone polymer having a K-value of 29–32 which may be obtained from ISP Technologies Inc., Wayne, New Jersey, USA, under the trademark PLASDONE ® K-29/32. This product meets the specification for Povidone USP.
(c) Added but not retained.
(d) The hydroxypropyl methylcellulose utilized in this example was PHARMACOAT ® 606 which may be obtained from Shin-Etsu, Ltd., Japan and has a viscosity in the range of 4.5 to 8.0 cps, a methoxy content of 28 to 30% by weight and a hydroxypropoxy content of 7 to 12% by weight.

The above described immediate release composition was prepared by the following process: The active ingredient, povidone, dicalcium phosphate dihydrate, and portions of the microcrystalline cellulose and sodium starch glycolate were mixed in a mixer-granulator (for example, a Littleford MGT) for approximately 5 minutes. Purified water was added while mixing until a suitable mass was obtained. The wet granules were passed through a cone mill fitted with an appropriate screen (e.g. 6.35 mm) and then were dried in a fluidized bed dryer set at an inlet temperature of approximately 65° C. to a loss on drying level of less than 2.5% w/w. The dried granules were then passed through a suitable mill fitted with an appropriate screen (e.g. #20 mesh in a hammer mill). The granulation was combined in a blender (e.g. V-blender) with lactose and the remainder of the microcrystalline cellulose and sodium starch glycolate and was blended for approximately 5 minutes. The magnesium stearate was passed through a suitable mill fitted with an appropriate screen (e.g. 40 mesh) and then was added to the dry granulated material and blended for approximately 3 minutes. The blended mixture was then compressed into tablets using conventional rotary compression equipment. The tablets were then film coated using conventional drum coating equipment with an aqueous suspension of the film coating constituents (i.e. hydroxypropyl methylcellulose, polyethylene glycol 400, yellow ferric oxide and titanium dioxide) at an inlet temperature of approximately 80° C.

What Is Claimed Is:

1. A sustained release formulation comprising a gelling agent and 11-[4-[2-(2-hydroxyethoxy)ethyl]-1-piperazinyl]dibenzo-[b,f][1,4]thiazepine or a pharmaceutically acceptable salt thereof, together with one or more pharmaceutically acceptable excipients.

2. A sustained release formulation according to claim 1 wherein the gelling agent is hydroxypropyl methylcellulose.

3. A sustained release formulation according to claim 2 comprising about 5 to 50% by weight of a hydroxypropyl methylcellulose selected from the group consisting of (a) a hydroxypropyl methylcellulose having a viscosity of about 40 to 60 cps, a methoxy content of about 28 to 30% by weight and a hydroxypropoxy content of from about 7 to less than 9% by weight, (b) a hydroxypropyl methylcellulose having a viscosity of about 3,500 to 5,600 cps, a methoxy content of about 28 to 30% by weight and a hydroxypropoxy content of about 7 to 12% by weight, (c) a hydroxypropyl methylcellulose having a viscosity of about 80 to 120 cps, a methoxy content of about 19 to 24% by weight and a hydroxypropoxy content of from about 7 to less than 9% by weight and (d) a hydroxypropyl methylcellulose having a viscosity of about 3,500 to 5,600 cps, a methoxy content of about 19 to 24% by weight and a hydroxypropoxy content of about 7 to 12% by weight, or mixtures thereof; with the proviso that if the formulation contains a hydroxypropyl methylcellulose described under (d) above the total amount of hydroxypropyl methylcellulose present in the formulation must be greater than 25.8% by weight.

4. A sustained release formulation according to claim 3 comprising about 5 to 40% by weight of a hydroxypropyl methylcellulose selected from the group consisting of (a)–(d) or mixtures thereof.

5. A sustained release formulation according to claim 4 comprising about 8 to 35% by weight of a hydroxypropyl methylcellulose selected from the group consisting of (a)–(d) or mixtures thereof.

6. A formulation according to claim 5 comprising about 10 to 30% by weight of a hydroxypropyl methylcellulose selected from the groups (a)–(d) or mixtures thereof.

7. A formulation according to claim 6 comprising about 15 to 30% by weight of a hydroxypropyl methylcellulose selected from the groups (a)–(d) or mixtures thereof.

8. A formulation according to claim 7 wherein the one or more pharmaceutically acceptable excipients are selected from the group consisting of microcrystalline cellulose, lactose, magnesium stearate, sodium citrate and povidone.

9. A formulation according to claim 8 wherein the one or more pharmaceutically acceptable excipients are selected from the group consisting of (a) about 4 to 20% by weight of microcrystalline cellulose, (b) about 5 to 20% by weight of lactose, (c) about I to 3% by weight of magnesium stearate, (d) about 10 to 30% by weight of sodium citrate and (e) about 1 to 15% by weight of povidone.

10. A formulation according to claim 1 wherein 11 -[4-[2-(2hydroxyethoxy)ethyl]-1-piperazinyl]dibenzo[b,f][1,4]thiazepine is in the form of a hemifumarate salt.

11. A formulation according to claim 1 wherein one of the one or more pharmaceutically acceptable excipients is a pH modifier.

12. A formulation according to claim 11 wherein the pH modifier is sodium citrate.

13. A method of treating psychotic states or hyperactivity in a warm-blooded animal which comprises administering to said warm-blooded animal an effective amount of a formulation according to anyone of claims 1–12.

14. A process for preparing a formulation according to anyone of claims 1 or 2 which comprises mixing 11-[4-[2-(2-hydroxyethoxy)ethyl]-1-piperazinyl]dibenzo[[b,f][1,4]thiazepine, or a pharmaceutically acceptable salt thereof, a gelling agent and other excipients.

15. A process for preparing a formulation according to anyone of claims 1 or 2 which comprises:

(a) mixing 11-[4-[2-(2-hydroxyethoxy)ethyl]-1-piperazinyl]dibenzo[b,f][1,4]thiazepine, or a pharmaceutically acceptable salt thereof, a gelling agent and other excipients;

(b) wet granulating the mixed components;

(c) drying the mixture;

(d) milling the dried mixture;

(e) blending the mixture with a lubricant; and (f) compressing the blended mixture to form tablets.

* * * * *